(12) United States Patent
Coppens et al.

(10) Patent No.: US 11,707,375 B2
(45) Date of Patent: Jul. 25, 2023

(54) HEAD AND JAW IMMOBILIZATION DEVICE

(71) Applicant: Qfix Systems, LLC, Avondale, PA (US)

(72) Inventors: Daniel D. Coppens, Avondale, PA (US); John Damon Kirk, Ramsey, NJ (US); Kristin M. Powell, Elkton, MD (US); Sean F. McGrenaghan, Downingtown, PA (US); Franklin B. Ports, Jr., Conowingo, MD (US)

(73) Assignee: Qfix Systems, LLC, Avondale, PA (US)

( * ) Notice: Subject to any disclaimer, the term of this patent is extended or adjusted under 35 U.S.C. 154(b) by 0 days.

(21) Appl. No.: 17/690,887

(22) Filed: Mar. 9, 2022

(65) Prior Publication Data

US 2022/0192856 A1    Jun. 23, 2022
US 2023/0103282 A9    Mar. 30, 2023

Related U.S. Application Data

(62) Division of application No. 14/894,030, filed as application No. PCT/US2014/039764 on May 28, 2014, now abandoned.
(Continued)

(51) Int. Cl.
*A61F 5/37* (2006.01)
*A61B 90/16* (2016.01)
(Continued)

(52) U.S. Cl.
CPC ............ *A61F 5/3707* (2013.01); *A61B 90/14* (2016.02); *A61B 90/16* (2016.02); *A61B 90/18* (2016.02);
(Continued)

(58) Field of Classification Search
CPC ...... A61F 5/3707; A61F 5/37; A61F 5/05883; A61F 5/05891; A61F 2009/0035;
(Continued)

(56) References Cited

U.S. PATENT DOCUMENTS 3,602,913 A    9/1971 Neese
5,503,167 A *  4/1996 Wilson .................... A61F 9/029
                                          132/319
(Continued)

FOREIGN PATENT DOCUMENTS

CN    1684636 A      10/2005
FR    2919171 A1 *   1/2009   ............. A61B 90/17
(Continued)

OTHER PUBLICATIONS

Fortin et al. (FR-2919171-A1) (Translation).*
(Continued)

*Primary Examiner* — Victoria Hicks Fisher
(74) *Attorney, Agent, or Firm* — RatnerPrestia

(57) ABSTRACT

Methods of immobilizing the head of a patient include heating a thermoplastic mask preform to a formable temperature, forming the thermoplastic mask over at least a mouth of the patient, and pushing a mouth receiving end of a bite piece into a portion of the thermoplastic mask preform that is positioned over the mouth of the patient, which moves the portion of the thermoplastic mask preform into the mouth of the patient. The methods also include allowing the thermoplastic mask preform to cool from the formable temperature, causing the portion of the thermoplastic mask moved into the mouth of the patient to harden.

4 Claims, 11 Drawing Sheets

Related U.S. Application Data

(60) Provisional application No. 61/903,631, filed on Nov. 13, 2013, provisional application No. 61/827,777, filed on May 28, 2013.

(51) Int. Cl.
| | |
|---|---|
| *A61B 90/18* | (2016.01) |
| *A61B 90/14* | (2016.01) |
| *A61C 5/90* | (2017.01) |
| *A61B 90/00* | (2016.01) |
| *A61N 5/10* | (2006.01) |

(52) U.S. Cl.
CPC .......... *A61C 5/90* (2017.02); *A61B 2090/0811* (2016.02); *A61N 2005/1097* (2013.01)

(58) Field of Classification Search
CPC ........ A61F 5/058; A61F 5/0104; A61F 9/026; A61F 9/029; A61F 9/02; A61N 2005/1097; A61N 5/10; A61B 90/14; A61B 90/18; A61B 90/16; A61B 90/10; A61B 6/0421; A61B 6/501; A61B 13/00; A45D 44/12; A61C 5/82; A61C 5/80; A61C 5/90; A61C 5/00; A61C 5/007
USPC .......................................................... 128/845
See application file for complete search history.

(56) References Cited

U.S. PATENT DOCUMENTS

| | | | |
|---|---|---|---|
| 5,531,229 | A | 7/1996 | Dean et al. |
| 5,538,014 | A | 7/1996 | Wilson et al. |
| 5,865,196 | A | 2/1999 | Foote |
| 6,634,884 | B2 | 10/2003 | Phillips |
| 6,945,251 | B2 | 9/2005 | Woodburn, III |
| 7,290,548 | B2 | 11/2007 | Ungemach et al. |
| 7,461,657 | B2 | 12/2008 | Woodburn |
| 8,419,426 | B2 | 4/2013 | Paris et al. |
| 8,667,970 | B2 | 3/2014 | Podmore et al. |
| 9,414,896 | B2 | 8/2016 | Giffey et al. |
| 2002/0038659 | A1* | 4/2002 | Al-Kassim ............. A61B 90/17 128/845 |
| 2002/0108616 | A1 | 8/2002 | Woodburn, III |
| 2003/0082496 | A1 | 5/2003 | Fischer et al. |
| 2006/0005839 | A1* | 1/2006 | Woodburn .......... A61B 6/0421 128/206.29 |
| 2010/0291504 | A1 | 11/2010 | Paris et al. |
| 2011/0240040 | A1 | 10/2011 | Westbrook et al. |
| 2012/0012120 | A1 | 1/2012 | Giffey et al. |
| 2014/0261430 | A1 | 9/2014 | Davis |
| 2016/0095739 | A1 | 4/2016 | Coppens et al. |

FOREIGN PATENT DOCUMENTS

| | | | |
|---|---|---|---|
| FR | 2919171 | A1 | 1/2009 |
| WO | 3733541 | A1 | 9/1997 |
| WO | 2004032781 | A1 | 4/2004 |
| WO | 2014093938 | A1 | 12/2014 |

OTHER PUBLICATIONS

Bionix TruGuard Custom Tongue and Jaw Positioner, Mar. 8, 2016, 10 pages.
Chinese Office Action for Chinese Application No. 201480042655.3, dated Jun. 30, 2017, including English translation, 11 pages.
Chinese Office Action for Chinese Application No. 201480042655.3, dated May 21, 2018, with English translation, 23 pages.
Civco 2005-2006 Sourcebook, Medtec Radiation Oncology Accessories, 3 pages.
Civco Medical Solutions Patient Positioning, Fixation and Localization, 3 pages.
European Communication for European Application No. 14734999.7, dated Dec. 11, 2018, 5 pages.
Extended European Search Report for European Application No. 20 184 556.7, dated Oct. 29, 2020, 8 pages.
Final Office Action for U.S. Appl. No. 15/602,372, dated Dec. 16, 2020, 38 pages.
International Search Report for International Application No. PCT/US2014/039764, dated Aug. 28, 2014, 4 pages.
International Preliminary Report on Patentability for International Application No. PCT/US2014/039764, dated Jun. 30, 2015, 7 pages.
Lock Definition, Merriam Webster Dictionary, definition 3a, https://www.merriam-webster.com/dictionary/lock (2020), 13 pages.
Non Final Office Action for U.S. Appl. No. 15/602,372, dated Apr. 3, 2020, 55 pages.
"Opening", yourdictionary.com, https://www.yourdictionary.com/opening, Retrieved from the internet May 6, 2021, 7 pages.
Radiation Oncology 2010 Sourcebook, Civco Medical Solutions, 3 pages.
Radiation Oncology 2011 Sourcebook, Civco Medical Solutions, 3 pages.
The Free Dictionary by Farlex, "thermoplastic," downloaded at https://www.thefreedictionary.com/Thermoplastics, 2021, 1 page.
Truguard, Custom Tongue and Jaw Positioner, Bionix Radiation Therapy, 2018, 2 pages.
Entire patent prosecution history of U.S. Appl. No. 14/894,030, filed Nov. 25, 2015, entitled, "Head and Jaw Immobilization Device".
Non Final Office Action for U.S. Appl. No. 15/602,372, dated Mar. 2, 2022, 19 pages.

* cited by examiner

HEAD AND JAW IMMOBILIZATION DEVICE

This is a Divisional Application of U.S. application Ser. No. 14/894,030, filed Nov. 25, 2015, which is the U.S. National Phase application of PCT/US2014/039764, filed May 28, 2014, and claims the benefit of priority of U.S. Provisional Application No. 61/827,777, entitled HEAD AND JAW IMMOBILIZATION DEVICE, filed on May 28, 2013, and U.S. Provisional Application No. 61/903,631, entitled HEAD AND JAW IMMOBILIZATION DEVICE, filed on Nov. 13, 2013, the contents of each of these applications being incorporated herein by reference in their entireties for all purposes.

FIELD OF THE INVENTION

The invention relates to patient immobilization for radiation therapy and other uses.

BACKGROUND OF THE INVENTION

Immobilization of a patient's head is critical in various diagnostic and precise treatment procedures of a patient's head and neck region. A low melting temperature thermoplastic mask is often used to immobilize the patient. In order to limit movement of the patient, the thermoplastic material is typically softened in a warm water bath. The mask is then stretched over the patient's head. As the thermoplastic material cools to room temperature, the mask hardens, thereby restricting patient movement. While the hardened mask restricts movement, it does not take into account the patient's change in physical dimensions over time due to, for example, weight loss or gain.

U.S. Pat. No. 6,945,251 to Woodburn teaches an apparatus for securing a thermoplastic mask to a patient using a complex arrangement of several independent attachment pieces and plates and distinct fastener plates that connect through the thermoplastic mask. However, attachment to the flexible thermoplastic mask results in excessive play between the mask and the patient.

Thus, the need remains to more securely attach a thermoplastic mask to a patient and immobilize the head and mouth of the patient. Precise and repeatable patient immobilization is the objective of the invention.

SUMMARY OF THE INVENTION

Aspects of the invention include methods of immobilizing the head of patients. The methods include heating a thermoplastic mask preform to a formable temperature, forming the thermoplastic mask over at least a mouth of the patient, and pushing a mouth receiving end of a bite piece into a portion of the thermoplastic mask preform that is positioned over the mouth of the patient, which moves the portion of the thermoplastic mask preform into the mouth of the patient. The methods also include allowing the thermoplastic mask preform to cool from the formable temperature, causing the portion of the thermoplastic mask moved into the mouth of the patient to harden.

Further aspects of the invention include a device for immobilizing the head of humans. The devices include a bite piece that is configured to push a portion of a formable thermoplastic mask preform into the mouth of the human, with the bite piece having a mouth receiving end and an applicator end. The mouth receiving end immobilizes the head of the human when the human bites down on the mouth receiving end and the thermoplastic mask cools.

Additional aspects of the invention include systems for immobilizing the head of patients. The systems include a formable thermoplastic mask preform having a portion configured to be positioned over the mouth of a patient. The systems also include a bite piece configured to push the portion of the formable thermoplastic mask preform into the mouth of the patient. The bite piece can have a mouth receiving end and an applicator end. The mouth receiving end immobilizes the head of the patient when the patient bites down on the mouth receiving end.

Further aspects of the invention include a patient immobilizer assembly configured to immobilize the head of a patient. The assemblies include a thermoplastic mask formed to be positioned over the head of the patient, with the thermoplastic mask having a proximal surface configured to be positioned against the head of the patient and a distal surface. The assemblies also include a bite piece secured to the thermoplastic mask, with the bite piece having a mouth receiving end extending into a concave region of the thermoplastic mask and extending outwardly from the distal surface of the thermoplastic mask. The mouth receiving end of the bite piece immobilizes the head of the patient when the patient bites down on a portion of the thermoplastic mask corresponding to the mouth receiving end.

Other aspects of the invention include a head and mouth immobilization device for securing a thermoplastic mask to a patient and immobilizing the patient. The device includes a low melting temperature thermoplastic mask and a bite piece with a mouth receiving end for securing top front teeth and bottom front teeth of the patient. The mouth receiving end of the bite piece inserts from an outside of the thermoplastic mask, through the mask and into the mouth of the patient.

Additional aspects of the invention include methods of securing a thermoplastic mask to a patient and immobilizing the patient. The methods include heating a low temperature thermoplastic pre-mask sheet until flexible, placing the pre-mask sheet over a patient's head and face, stretching the pre-mask sheet over the head, face and mouth of the patient forming a mask, inserting a bite piece through the thermoplastic mask and into the patient's mouth, closing the patient's mouth and engaging the bite piece with the top front teeth and bottom teeth (e.g., the mouth, the jaw, the mandible, the maxilla, etc.), and cooling the mask to room temperature thereby hardening the mask so that the bite piece is in a fixed position in relation to the mask and the patient's mouth.

DESCRIPTION OF EMBODIMENTS OF THE INVENTION

Figure 1:
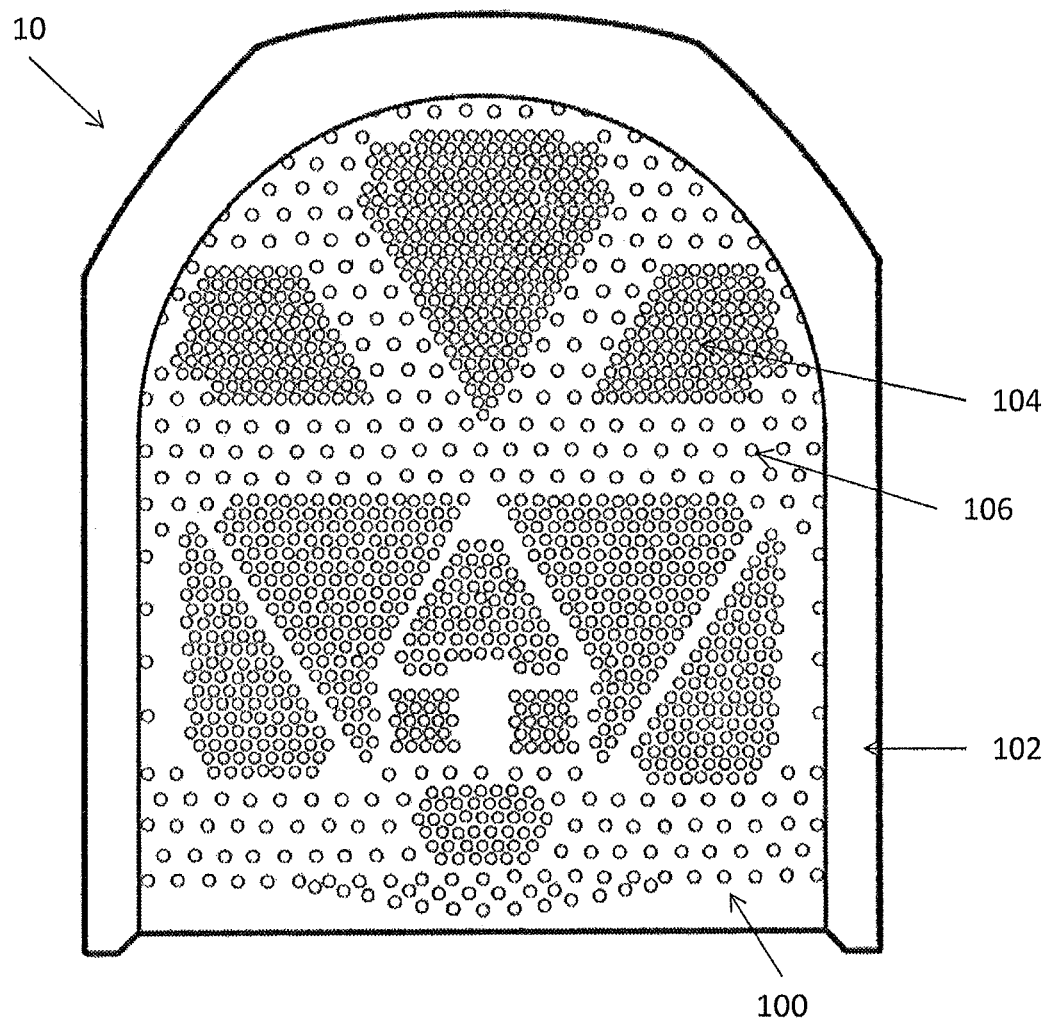
FIG. 1 illustrates a unformed pre-mask sheet for use as a patient immobilization mask according to aspects of the invention.

Although the invention is illustrated and described herein with reference to specific embodiments, the invention is not intended to be limited to the details shown. Rather, various modifications may be made in the details within the scope and range of equivalents of the claims and without departing from the scope of the invention.

The invention solves the aforementioned problems and provides a head and mouth immobilization device for securing a thermoplastic mask to a patient and immobilizing the patient's head. It includes a low melting temperature thermoplastic mask and a bite piece with a mouth receiving end for securing the mouth of the patient. The mouth receiving end of the bite piece inserts from the outside (non-patient side, distal surface) of the thermoplastic mask, and pushes a portion of the mask into the patient's mouth.

Referring to the figures generally, the invention provides preforms, such as preforms 10, 20, and 1200, used to be formed into an immobilizer with bite pieces, such as bite pieces 30, 60, 90, 1000 and 1202 for use with a patient. The preforms and bite pieces may be bundled together as a kit for immobilizing the head and mouth of a patient. The preform includes a preform member, such as preform member 100, that is formed from a thermoplastic material. The preform member is relatively rigid at a first temperature and formable at an elevated second temperature.

The bite pieces may include applicator ends, such as applicator ends 300, 600, 900 and 1002, and mouth receiving ends, such as mouth receiving ends 302, 602, 902 and 1004. The applicator ends are used to push the mouth receiving end into a portion of the thermoplastic preform member that is positioned over the mouth of the patient. The mouth receiving ends push the preform member that is positioned over the mouth of the patient into the mouth of the patient, which then immobilizes the mouth (e.g., the upper and lower teeth, the jaw, the maxilla, the mandible, etc.) of the patient when the preform member cools from the formable temperature.

The bite pieces may also be separable, such that the applicator end may be separated from the mouth receiving end when the mouth receiving end is fixed to the mouth of the patient. The applicator ends can be separated by snapping, cutting, or sliding transversely with respect to the mouth receiving end. The applicator end and mouth receiving end may be formed from the same integrated piece or may be separate pieces.

Referring to FIG. 1, a preform 10 with a preform member 100 formed from thermoplastic material formable to a patient's anatomy is shown. In one embodiment, the thermoplastic material includes a Polycaprolactone-based (PCL) low temperature thermoplastic. The preform member 100 is made of a thermoplastic material such that it can be heated to a formable temperature to be formed to a patient's anatomy, and then cooled to become rigid and act as a patient immobilizer. The preform member includes a proximal surface that contacts the head of the patient, and a distal surface opposite of the proximal surface. The distal surface receives the bite piece, as is described further below.

Polycaprolactone (PCL) based low temperature thermoplastics are suitable for use in a wide range of medical applications such as splinting, casting and molding for applications in Radiation Therapy and Orthopedics. The material is typically heated in a water bath or in an oven or by other application of heating energy to its melting point and is then formed to the patient's anatomy to make a custom formed device (e.g., around the head of a patient). The material is optionally partially cross-linked prior to heating. Such partial cross-linking improves the usability of the preform member.

The preform member 100 may optionally include at least one filler material together with the thermoplastic base material. In order to improve the physical performance of the PCL material (i.e. stiffness and strength) as well as for aesthetic reasons, it is often desirable to add fillers to these materials. Fillers can include, but are not limited to, materials such as talc, aramid (KEVLAR®), dyes, nanoparticles, carbon fiber, fiberglass, polyurethane, fumed silica, high stiffness additives, etc.

Additionally, a thermochromic dye is optionally added to the base material or to the frame 102. For such a dye, a transition temperature can be selected that is near, above or below the softening temperature of the base material. Also, the dimensions of the base material and temperature characteristics of such a dye can be selected such that a temperature change of the surface of the base material would match the actual core temperature of the base material.

The preform 10 includes the preform member 100 that is positioned within a frame member 102. In many applications the PCL thermoplastic preform member 100 is mounted to a rigid thermoplastic (TP) frame member 102 (typically formed from ABS or another suitable material). The frame member 102 is preferably formed from a material that does not soften when heated to 140F (i.e., approximately the temperature at which the preform member 100 can be molded), the melting point of PCL. This allows the assembly (i.e., preform 10) to be mounted to various other devices. The preform 10 is perforated, and includes perforated sections 104 and 106 of various perforation patterns that allow for greater custom formability to a patient's anatomy. Various perforation patterns may be used to effectuate this feature.

Figure 2:
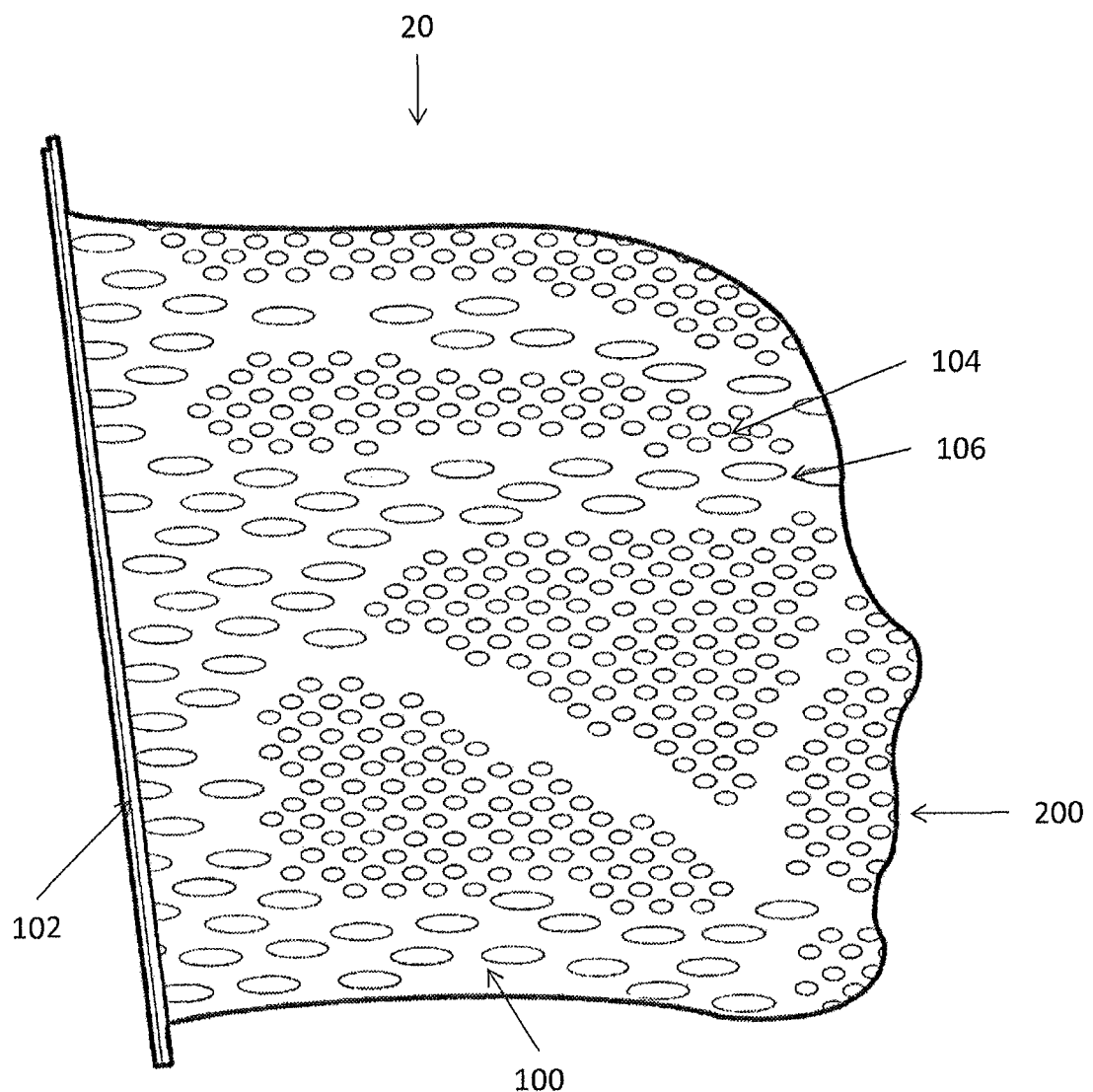
FIG. 2 depicts a side view of a patient immobilization mask formed to the head of a patient before the bite piece is added in accordance with aspects of the invention.

Referring next to FIG. 2, the preform member 100 of the preform 10 is shown as a molded preform 20 over the head of a patient. In an embodiment as shown, the preform member 100 includes a portion 200 that is molded/positioned over the mouth of the patient.

Figure 3:
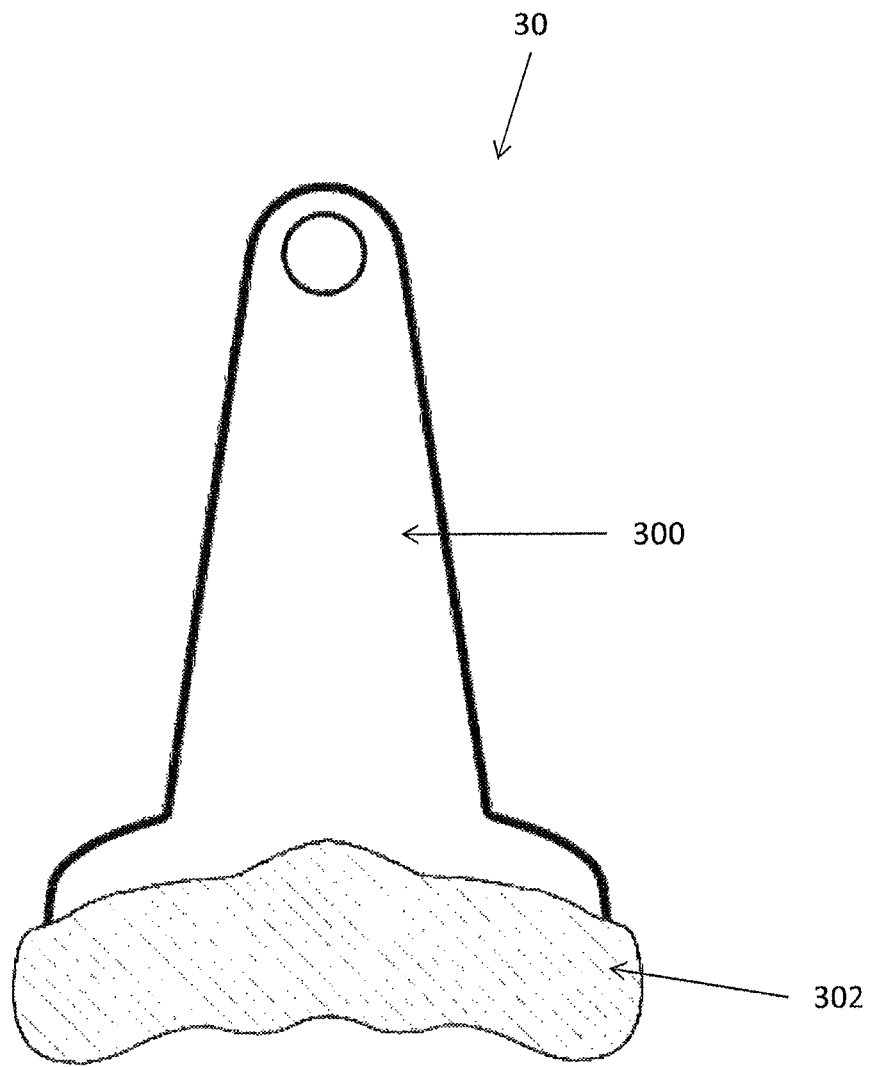
FIG. 3 depicts an example of a bite piece according to aspects of the invention.

FIG. 3 depicts a bite piece according to an embodiment of the invention. The bite piece 30 includes an applicator end 300 and a mouth receiving end 302. The mouth receiving end 302 may include a piece of thermoplastic material (e.g., PCL) applied to the end 302 to adhere to the preform when pushed into the preform thermoplastic mask. The applicator end 300 is connected to the mouth receiving end 302 and may be used to guide the mouth receiving end 300 into a thermoplastic mask (e.g., preform 10) and into a portion of the thermoplastic mask formed over the mouth of a patient, pushing the portion of the thermoplastic mask into the mouth of the patient. More specifically, the bite piece 30 may adhere and harden in a fixed position to the thermoplastic mask securing the patient's mouth, thereby providing superior head immobilization. The bite piece 30 may immobilize the patient's mouth by securing various parts of the mouth such as, for example, the jaw, the upper teeth, the lower teeth, the mandible, etc. In an embodiment, the bite piece 30 immobilizes the patient's maxilla when pushing the portion 200 of the thermoplastic mask into the mouth of the patient. Other parts of a patient's mouth or other anatomy capable of being secured by bite pieces will be understood by one of skill in the art from the description herein.

Immobilization of the patient using the invention is not only precise but reproducible. The material of the bite piece 30 may be chosen from a variety of materials including but not limited to acrylonitrile butadiene styrene (ABS), polyethylene terephthalate (PETG), nylon, and polyvinyl chloride (PVC). This material can be chosen so that it will stick to the thermoplastic mask as it cools providing a secure fixation. Alternatively, the material may be chosen such that the mouth receiving end 302 (with the attached thermoplastic) will stick to the thermoplastic mask but the applicator end 300 will not. The bite piece may be designed to allow the portion that remains outside the patient's mouth (e.g., the applicator end 300) to be removed, as is described at FIGS. 6-14. Techniques for doing this include but are not limited to cutting, snapping, sliding, etc. The bite piece may also contain a piece of PCL (at the mouth receiving end, e.g., mouth receiving end 302), this aids in the bonding of the bite piece to the thermoplastic mask.

Figure 4:
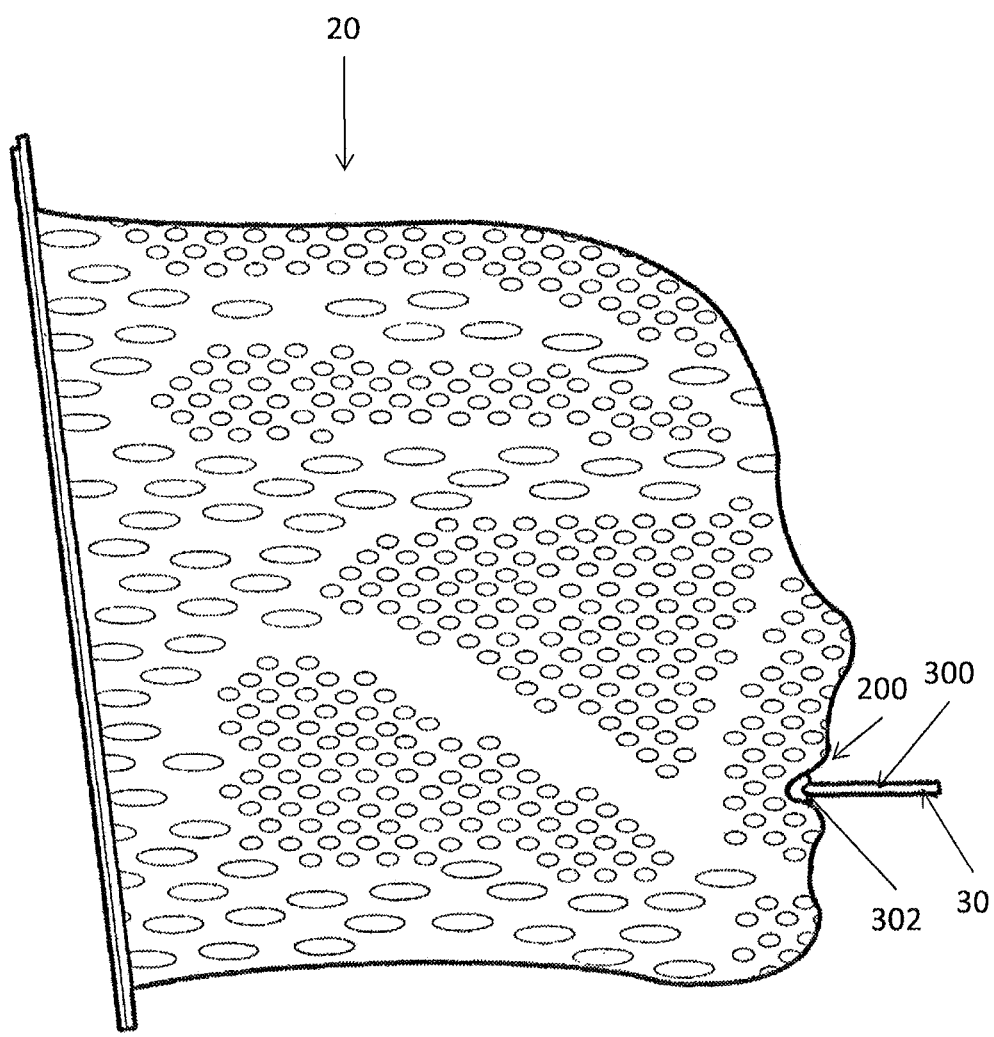
FIG. 4 is a side view of the patient immobilization mask formed to the head of a patient with a bite piece applied to the mask in accordance with aspects of the invention.
Figure 5:
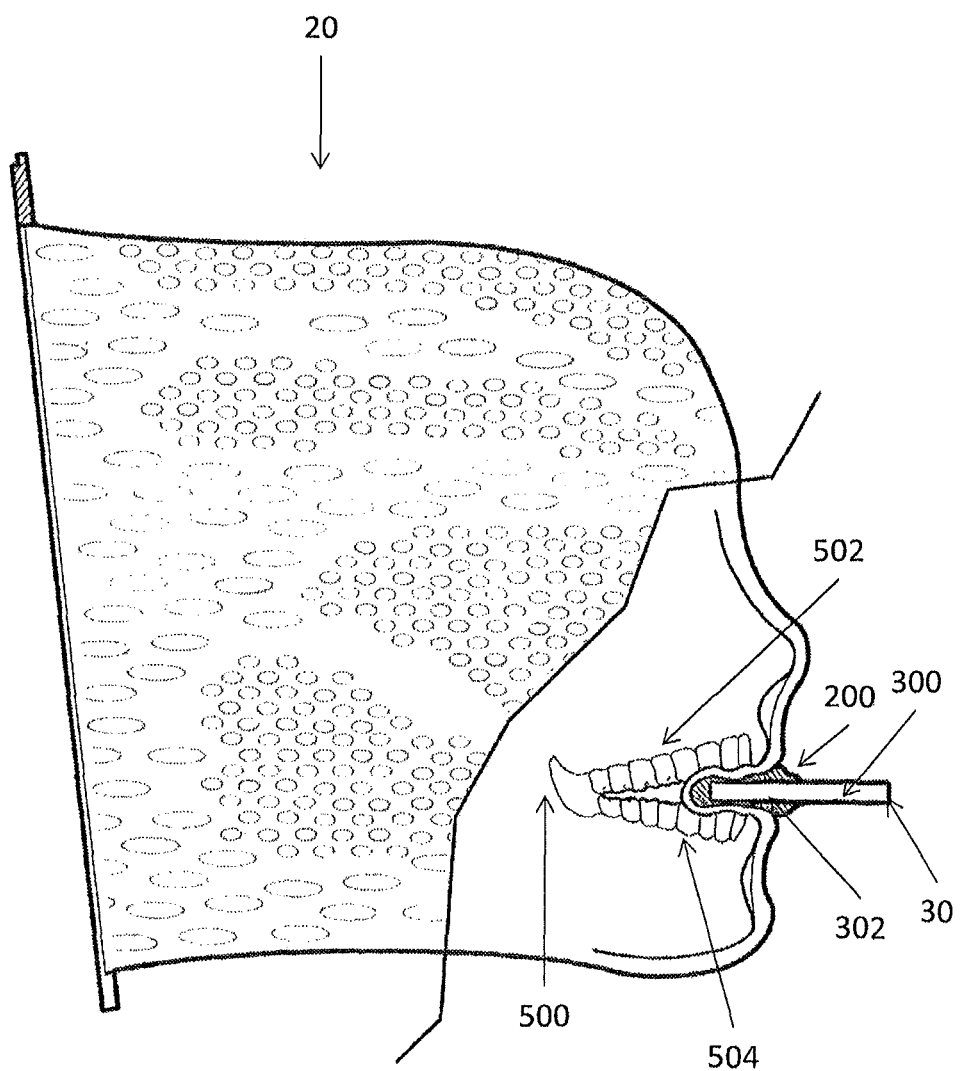
FIG. 5 is a cut-away side view of the mouth of a patient through a patient immobilization mask formed over the head of the patient according to aspects of the invention.
Figure 6:
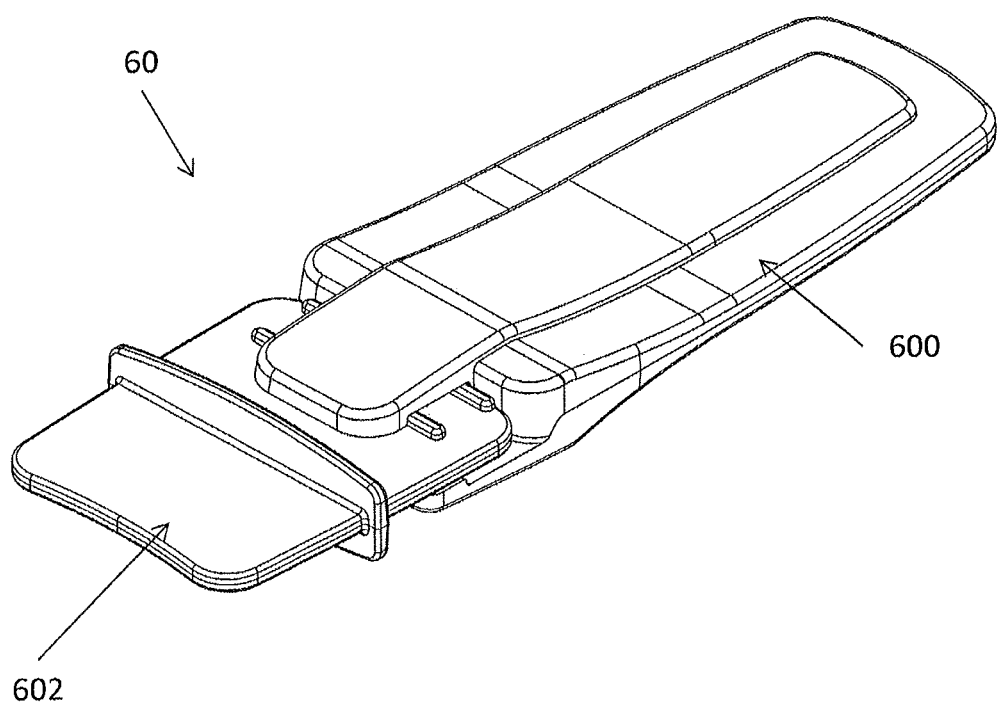
FIG. 6 illustrates an embodiment of a bite piece assembly according to aspects of the invention.

FIGS. 4 and 5 depict the bite piece pushed through a thermoplastic mask according to aspects of the invention. The preform 20 is formed over the head of the patient. The bite piece 30 is positioned at the portion 200 of the preform that is positioned over the mouth of the patient. As shown in FIG. 5, the mouth receiving end 302 pushes the section 200 of the preform 20 into the mouth 500 of the patient. As the patient bites down on the bite piece 30, the top teeth 502 and optionally the bottom teeth 504 of the patient mouth mold the portion 200, and as the thermoplastic preform 20 hardens when cooled to room temperature, the teeth 502 and 504, the maxilla, and optionally the mandible of the mouth 500 are immobilized.

The bite piece can also be of a separable two piece design as shown in FIGS. 6-14. Referring generally to FIGS. 6-9, the bite piece 60 includes an applicator end 600 and a mouth receiving end 602. The applicator end 600 is separable from the mouth receiving end 602. This allows one piece (e.g., the mouth receiving end 602) of the bite piece to be inserted, at least partially, into the patient's mouth. The second piece (e.g., the applicator end 600) of the bite piece can be removed; this will minimize the material protruding from the mask. This has advantages for ease of storage and use. It also ensures that this material (e.g., the material from which the bite piece 60 is made) will not interfere with optical tracking systems which monitor the position of anatomical reference features near the patient's nose and eyes.

Figure 9:
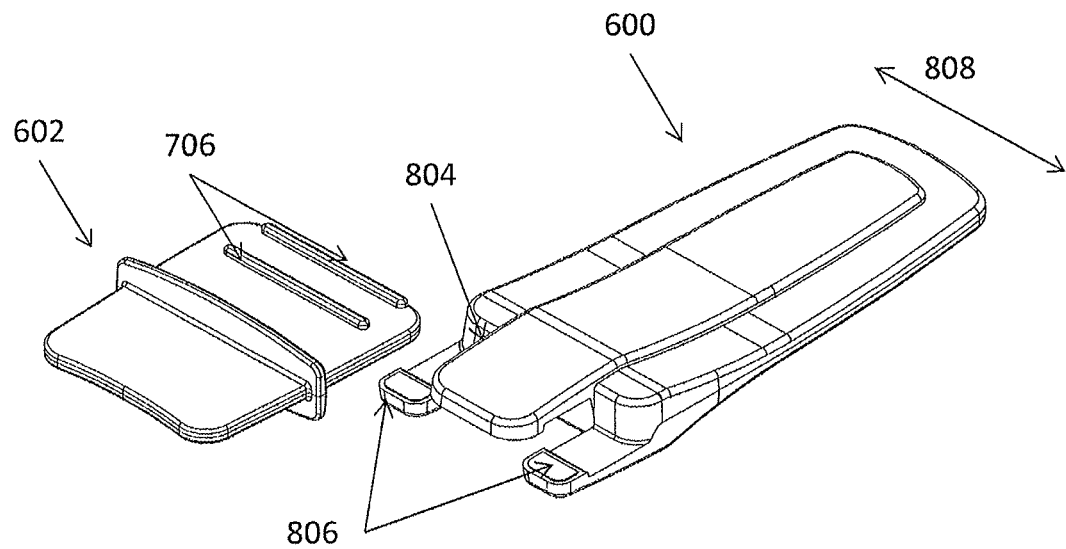
FIG. 9 illustrates components of the bite piece assembly shown in FIG. 6 as they are separated in accordance with aspects of the invention.

This second piece (e.g., the applicator end 600) may be removable using a variety of methods including but not limited to clipping on/off, sliding, etc. When the applicator end 600 is separated from the mouth receiving end 602, the mouth receiving end 602 may extend from the distal surface of the thermoplastic mask to a distance so as to reduce interference with a camera of a visual tracking system. In an embodiment, the mouth receiving end extends less than about an inch from the distal surface of the mask. Additionally, the bite piece, including the applicator end and the mouth receiving end, may extend less than about one inch from the distal surface of the mask. As depicted in FIG. 9, an embodiment in which the applicator end 600 slides horizontally (e.g., transversely with respect to the mouth receiving end 502, along axis 808) to be removed is shown. This allows the applicator end 600 to be removed without exerting a substantial force on the patient. The second piece (e.g., applicator end 600) of the bite piece may be constructed from a material that will not stick to the thermoplastic mask. These materials include but are not limited to nylon, acetal, etc.

Figure 7:
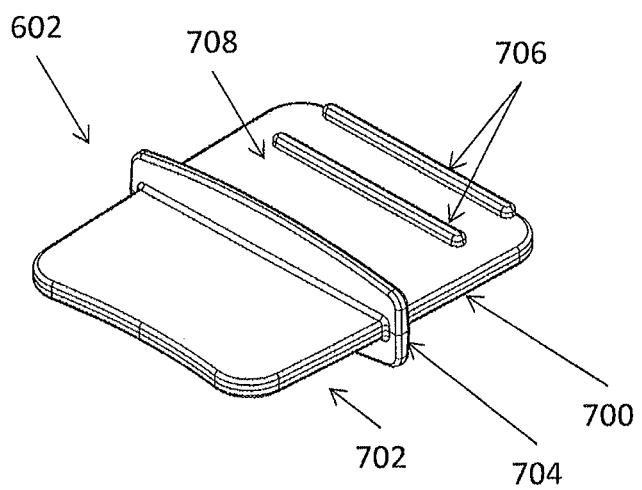
FIG. 7 illustrates a component of the bite piece assembly shown in FIG. 6 in accordance with aspects of the invention.

As depicted in FIG. 7, the mouth receiving end 602 of the bite piece may comprise a proximal portion 702 and a distal portion 700, separated by a depth indicator 704. The proximal portion 702 may be configured to contact a distal surface of a thermoplastic mask (e.g., preform 10, 20) to push the mask into the mouth of the patient and immobilize the patient. The distal end 700 is configured to attach to the applicator end 600 of the bite piece 60 and includes projections 706 on the upper surface 708 that may be used to attach to the applicator end 600. In an embodiment, similar projections are included on the bottom surface of the distal end 700. The depth indicator 704 may be configured such that the user (e.g., medical professional) can easily identify the depth that the bite piece 60 has been inserted in the patient's mouth. It is contemplated that the depth indicator 704 may be positioned on the applicator end 600 of the bite piece 60 in place of or in addition to being positioned on the mouth receiving end 602. As depicted, the depth indicator 704 is a projection that extends around a portion or all of the perimeter of the mouth receiving end 602. This depth indicator 704 may also be accomplished using one or more ridges or by using a scale. This indicator 704 will allow the user to ensure that they have inserted the bite piece 60 to a depth sufficient to allow for secure fixation of the patient.

Figure 8:
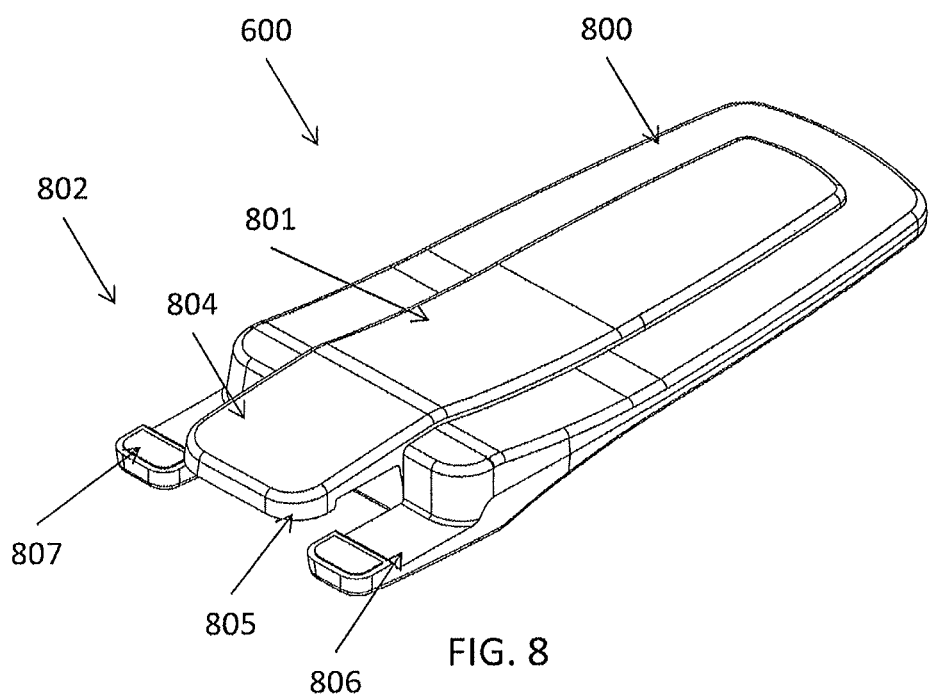
FIG. 8 illustrates another component of the bite piece assembly shown in FIG. 6 according to aspects of the invention.

As shown in FIG. 8, the applicator end 600 includes a distal end 800 and a proximal end 802. The distal end 800 is elongated and is configured to be gripped, such that the bite piece 60 can be pushed into the thermoplastic mask. The distal end 800 may also include a curved portion 801 to facilitate grip of the applicator end 600 during insertion and separation of the bite piece 60. The proximal end 802 is configured to engage the distal end 700 of the mouth receiving end 602 of the bite piece 60. The proximal end 802 includes a top flange 804 that extends over the projections 706 on the top surface 708 of the mouth receiving end 602. The top flange 804 has a downward extending projection 805 that extends past the projections 706 when the applicator end 600 is attached to the mouth receiving end 602, preventing separation of the ends 600 and 602 when the bite piece 60 is being pushed to the thermoplastic mask. In an embodiment, the proximal end 802 also includes a series of bottom flanges 806 with upward facing projections 807 configured to engage projections on the bottom surface of the mouth receiving end 602 (not shown) similarly to the engagement of the top flange 804 with the projections 706.

The arrangement of the flanges 804, 806 and projections 706, 805, 807 provide that the applicator end 600 is separable from the mouth receiving end 602 by moving the applicator end 600 transversely with respect to the mouth receiving end 602. The arrangement also provides that the ends 600 and 602 of the bite piece 60 remain attached and resist axial forces when the bite piece 60 is pushed into the thermoplastic mask.

Figure 10:
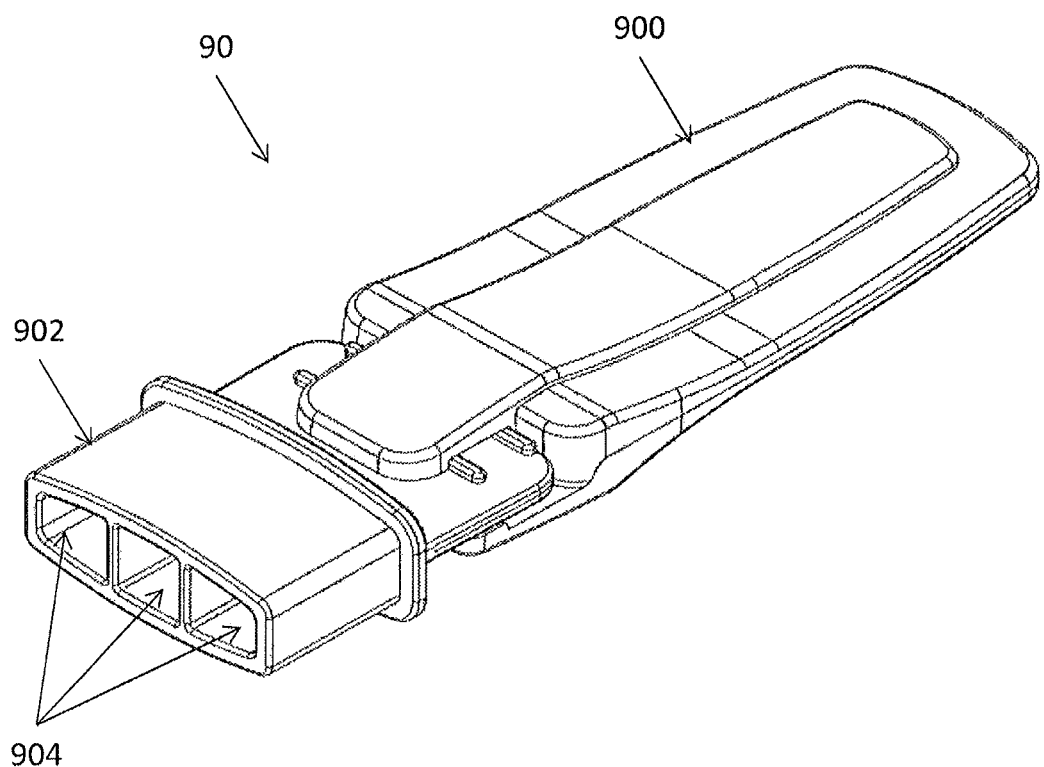
FIG. 10 illustrates an embodiment of a bite piece in accordance with aspects of the invention.
Figure 11:
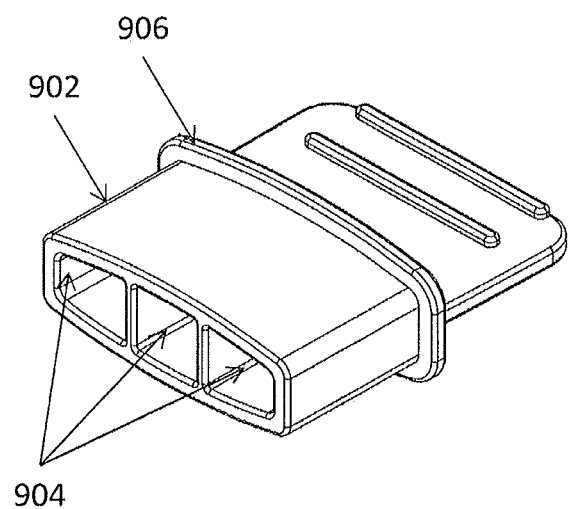
FIG. 11 illustrates another embodiment of a component that can be used with the bite piece assembly shown in FIG. 10 according to aspects of the invention.
Figure 12:
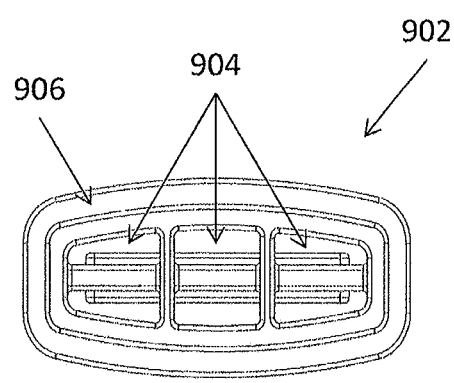
FIG. 12 is a front view of a component that can be used with the bite piece assembly shown in FIG. 10 according to aspects of the invention.

In an embodiment as shown in FIGS. 10, 11 and 12, a bite piece 90 includes a mouth receiving end 902 with air channels 904 to facilitate the breathing of the patient. In order to provide an air passage to allow the patient to breathe easily the bite piece may be configured as shown in FIGS. 10, 11 and 12. The bite piece 90, as well as the applicator end 900 and the mouth receiving end 902 may function substantially as applicator end 600 and mouth receiving end 602, with the addition of the air channels 904 in the mouth receiving end 902. The air channels 904 extend through the mouth receiving portion 902 to the depth indicator 906, such that air can pass to and from the patient through the channels 904. The air channels 904 may extend through to any portion of the bite piece 90 provided an opening on each end of the air channels 904 to facilitate passing air. Air channels 904 may be molded into the bite piece to provide a path for air to travel from the ambient environment to the patient's mouth.

Figure 13:
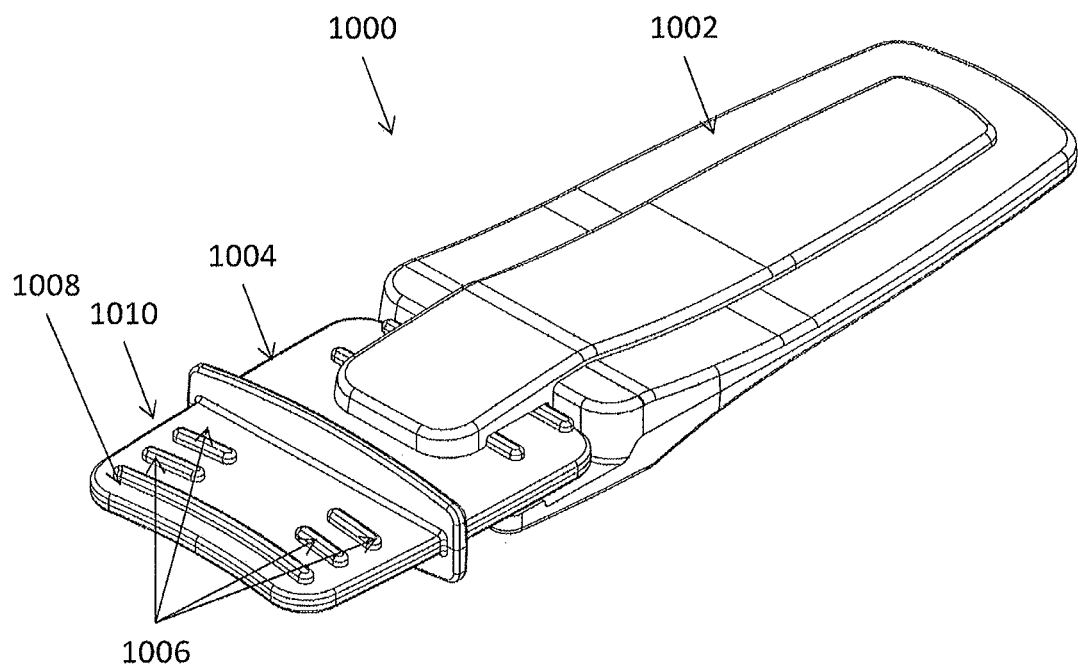
FIG. 13 illustrates an embodiment of a bite piece in accordance with aspects of the invention.
Figure 14:
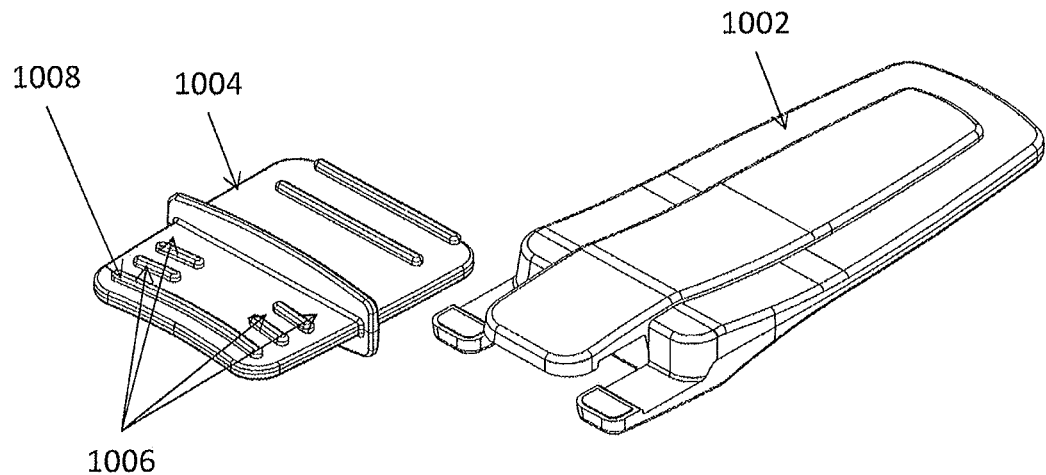
FIG. 14 illustrates components of a bite piece according to aspects of the invention.

FIGS. 13 and 14 depict another embodiment of a bite piece according to aspects of the invention. The bite piece 1000 includes an applicator end 1002 and a mouth receiving end 1004. The applicator end 1002 functions similar to the applicator end 600. The mouth receiving end 1004 functions similar to the mouth receiving end 602 except that the mouth receiving end 1004 additionally includes ribs 1006 and 1008 on the surface of the proximal end 1010 of the mouth receiving end 1004. The ribs 1006 and 1008 may form a mechanical lock with the thermoplastic mask. In an embodiment, the bite piece 1000 is pushed against the distal surface of a thermoplastic mask, forming a concave region where the mask is formed over the mouth of a patient. The mouth receiving end 1004 pushes the proximal surface of the mask into the mouth of the patient. Once the patient bites down on the mouth receiving end 1004, the portion of the thermoplastic mask pushed into the mouth of the patient forms over the ribs 1006 and 1008 and thus forms a mechanical lock when the mask is allowed to cool and become rigid. Although depicted as horizontal, the ribs 1006 and 1008 may be of any shape capable of forming a mechanical lock upon contact and cooling with a thermoplastic mask, such as curved or cross-shaped.

Figure 15:
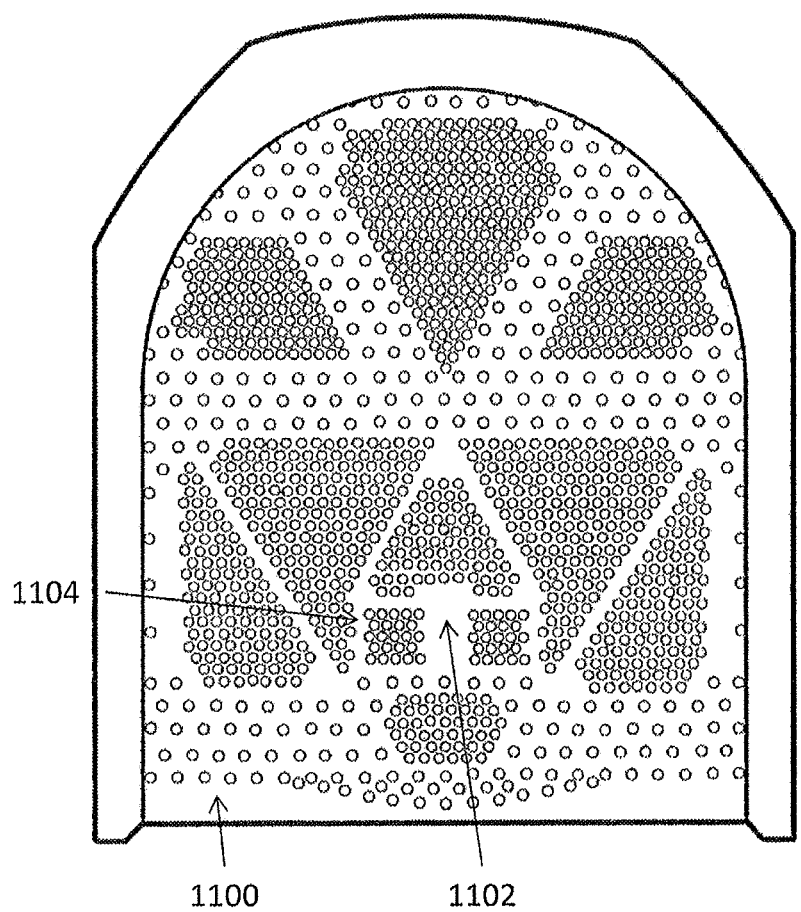
FIG. 15 illustrates a pre-mask sheet with an area of non-stick coating in the area where the bite piece is to be inserted in accordance with aspects of the invention.

Referring next to FIG. 15, as another example, by configuring a bite piece and providing perforations 1102 in a thermoplastic mask 1100 in the region 1104 covering the mouth, air may pass freely to the patient via the perforations 1102. In an embodiment, the perforations 1102 are used with mouth receiving ends 902 with air channels 904 to facilitate breathing of the patient while the patient is immobilized. Alternatively or additionally, any combination of air channels 904 of the bite piece or perforations 1102 over the region 1104 covering the mouth of the patient may be used to facilitate breathing of the patient when the patient is immobilized.

Figure 16:
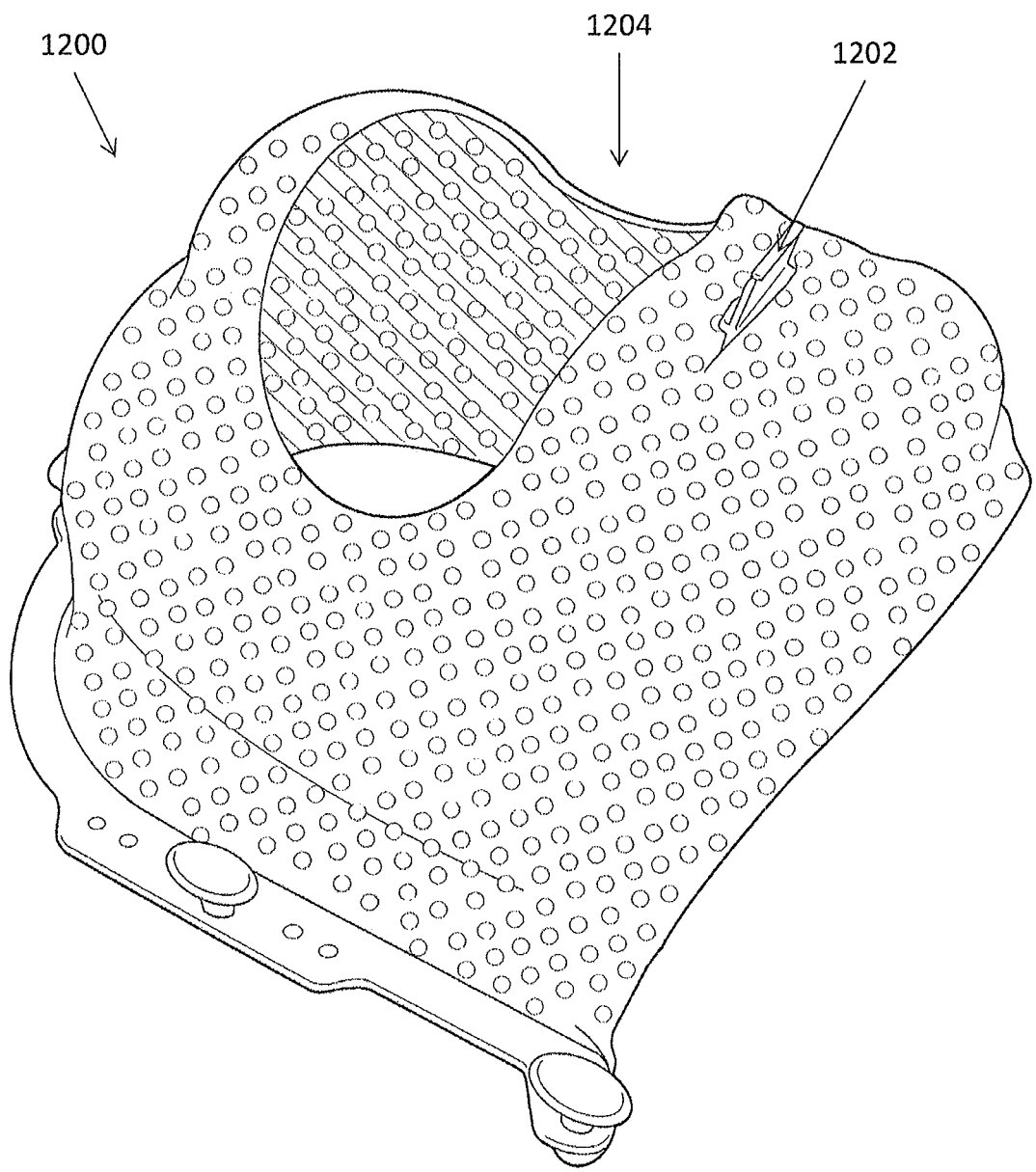
FIG. 16 illustrates another embodiment of a patient immobilization mask formed over the head of a patient with a bite piece applied according to aspects of the invention.

In another embodiment is shown in FIG. 16, a preform 1200 is formed to the head of a patient. The patient is immobilized with the preform 1200 and the bite piece 1202. In this embodiment the mask (e.g., preform 1200) contains one or more larger openings 1204 in the area of the patient's nose and eyes. The opening 1204 are constructed to be larger than other perforations in the mask such that either the eyes or the nose, or both, of the patient fit through the opening 1204. This provides advantages for patients who are claustrophobic as well as allowing the mask (e.g., preform 1200) to be used with optical tracking systems used in radiation therapy. These tracking systems often use anatomical reference features in the area of the patient's nose and eyes. By providing a mask that is open in this area the optical tracking systems may be used. Because the crown of the patient's head is indexed and restrained as well as their pallet this mask provides superior patient restraint over other open masks.

In embodiments where the bite piece includes separable components, the mouth receiving portion of the bite piece that remains immobilizes the patient's mouth has two ends. The first proximal end (e.g., proximal end 702, 1010) resides in the patients mouth and the distal end (e.g., distal end 708) protrudes and extends outwardly from a concave region formed upon pushing the thermoplastic mask into the mouth of the patient. The geometry of the two ends can be different to prevent a user from pushing the wrong end against the thermoplastic mask. Ribs (such as ribs 1006 and 1008) may be used to prevent the applicator from being attached to the wrong end, as well as different colors in order to distinguish the two ends of the mouth receiving end.

Methods for immobilizing a patient with a thermoplastic mask and a bite piece are now described in accordance with embodiments of the invention. The preform/thermoplastic mask includes a preform member that is relatively rigid at a first temperature and is formable at a second, formable temperature.

First, the thermoplastic mask is heated to the formable temperature. The formable temperature may be a temperature at which the mask can be formed to the anatomy of the patient, preferably the head of a patient.

Second, the thermoplastic mask that is heated to the formable temperature is formed over at least the mouth of the patient. The mask may be formed by pushing the head of the patient into the mask when the mask is at a formable temperature and/or pulling the mask over the head of the patient. Preferably, the mask is formed over the mouth of the patient.

Next, a mouth receiving end of a bite piece is pushed into a portion of the thermoplastic mask that is positioned over the mouth of the patient. The portion of the mask that is positioned over the mouth of the patient may be a concave portion that is formed into a concave shape as a result of being formed to the mouth of the patient. Pushing the mouth receiving end of the bite piece into the portion moves the portion of the thermoplastic mask preform into the mouth of the patient. Once this portion is pushed into the mouth of the patient, the patient preferably bites down on the portion, causing the portion to form to the teeth, maxilla, mandible, jaw, etc., of the patient and to affix to the mouth receiving end of the bite piece. The mouth receiving end may be pushed into the portion to a depth indicated by a depth indicator formed on the surface of the mouth receiving end of the bite piece.

After the mouth receiving end of the bite piece is pushed, moving the portion of the thermoplastic mask into the mouth of the patient, the thermoplastic mask preform may be allowed to cool, thereby causing the portion moved into the mouth of the patient (and the remainder of the thermoplastic mask) to harden, immobilizing the patient and providing superior immobilization as compared to masks which do not use bite pieces as described above. The thermoplastic mask preform may be allowed to cool to room temperature, although the desired temperature at which allow the mask to cool may depend on the material from which the mask is constructed as is known to those of skill in the art. In an embodiment where the bite pieces include an applicator end that is separable from the mouth receiving end, the applicator end may be separated from the mouth receiving end when the mask is hardened and the mouth receiving end is affixed.

What is claimed:

1. A method of immobilizing the head of a patient, the method comprising the steps of:
   heating a thermoplastic mask preform to a formable temperature;
   forming the thermoplastic mask preform over at least a mouth of the patient;
   pushing a mouth receiving end of a bite piece into a portion of the thermoplastic mask preform that is positioned over the mouth of the patient, thereby moving the portion of the thermoplastic mask preform into the mouth of the patient; and
   allowing the thermoplastic mask preform to cool from the formable temperature, thereby causing the portion of the thermoplastic mask preform to harden.

2. The method of claim 1, wherein the pushing step includes pushing the mouth receiving end of the bite piece into the portion of the thermoplastic mask preform via an applicator end of the bite piece.

3. The method of claim 2, further comprising separating the applicator end of the bite piece from the mouth receiving end of the bite piece.

4. The method of claim 1, wherein the pushing step further comprises pushing the mouth receiving end of the bite piece to a depth indicated by a depth indicator formed on the bite piece.

* * * * *